United States Patent
Reuter et al.

(10) Patent No.: US 9,307,770 B2
(45) Date of Patent: *Apr. 12, 2016

(54) BACILLUS LICHENIFORMIS STRAIN

(71) Applicant: Osprey Biotechnics, Inc., Sarasota, FL (US)

(72) Inventors: Christopher J. Reuter, Parrish, FL (US); Steven J. MacKenzie, Sarasota, FL (US); Lauren G. Danielson, Bradenton, FL (US); Vincent Scuilla, Sarasota, FL (US)

(73) Assignee: Osprey Biotechnics, Inc., Sarasota, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/211,718

(22) Filed: Mar. 14, 2014

(65) Prior Publication Data

US 2015/0257391 A1   Sep. 17, 2015

(51) Int. Cl.
 *A62D 3/00*   (2007.01)
 *A01N 63/00*  (2006.01)
 *C12R 1/10*   (2006.01)
 *A01N 25/00*  (2006.01)
 *A23L 3/3571* (2006.01)
 *C02F 3/34*   (2006.01)

(52) U.S. Cl.
 CPC .............. *A01N 63/00* (2013.01); *A01N 25/00* (2013.01); *A23L 3/3571* (2013.01); *C12R 1/10* (2013.01); *C02F 3/34* (2013.01)

(58) Field of Classification Search
 CPC ............. A01N 63/00; C12R 1/10; A62D 3/02
 See application file for complete search history.

(56) References Cited

U.S. PATENT DOCUMENTS

| | | | |
|---|---|---|---|
| 6,025,187 A  * | 2/2000  | Penaud  | ....................... 435/262.5 |
| 8,236,549 B2  | 8/2012  | Kang et al. | |
| 8,338,160 B2  | 12/2012 | Tzeng et al. | |
| 8,377,455 B2  | 2/2013  | Ceri et al. | |
| 8,404,476 B2  | 3/2013  | Fernandez Martinez et al. | |

FOREIGN PATENT DOCUMENTS

CN          103243041 A   *   8/2013

OTHER PUBLICATIONS

STN abstract for CN 103243014 (publication date Aug. 14, 2013) downloaded from CAPLUS Apr. 5, 2015.*
Wentz, M. Science (1967) 155: 89-90.*
Machine translation of CN 103243041 A published Aug. 14, 2013.*

* cited by examiner

*Primary Examiner* — Susan Hanley
(74) *Attorney, Agent, or Firm* — Butzel Long

(57) ABSTRACT

The invention related to the use of *Bacillus licheniformis* strain OBT618 (ATCC PTA-122188) for inhibiting *Clostridium* pathogens in a material contaminated with the pathogens. The strain can be added to animal feed, animal waste or food processing facility waste that is contained with *Clostridium* to inhibit the pathogen.

2 Claims, 1 Drawing Sheet

```
                    B licheniformos-OBT618-16S-rRNA-seq fasta
>B.licheniformos OBT618
TGGAGAGTTTGATCCTGGCTCAGGACGAACGCTGGCGGCGTGCCTAATACATGCAAGTCGAGCGGACCGACGGGAGCTTGCTCC
CTTAGGTCAGCGGCGGACGGGTGAGTAACACGTGGGTAACCTGCCTGTAAGACTGGGATAACTCCGGGAAACCGGGGCTAATAC
CGGATRCTTGATTGAACCGCATGGTTCAATTATAAAAGGTGGCTTTTAGCTACCACTTACAGATGGACCCGCGGCGCATTAGCT
AGTTGGTGAGGTAACGGCTCACCAAGGCAACGATGCGTAGCCGACCTGAGAGGGTGATCGGCCACACTGGGACTGAGACACGGC
CCAGACTCCTACGGGAGGCAGCAGTAGGGAATCTTCCGCAATGGACGAAAGTCTGACGGAGCAACGCCGCGTGAGTGATGAAGG
TTTTCGGATCGTAAAACTCTGTTGTTAGGGAAGAACAAGTACCGTTCGAATAGGGCGGTACCTTGACGGTACCTAACCAGAAAG
CCACGGCTAACTACGTGCCAGCAGCCGCGGTA
```

BACILLUS LICHENIFORMIS STRAIN

CROSS-REFERENCE TO RELATED APPLICATIONS

Not Applicable.

FIELD OF THE DISCLOSURE

This disclosure concerns a *Bacillus licheniformis* strain useful for inhibiting the growth of pathogens.

BACKGROUND OF THE DISCLOSURE

*Bacillus licheniformis* bacterium is a gram-positive, mesophilic bacterium that is commonly found in the soil and on bird feathers, especially on the chest and back plumage of ground-dwelling and aquatic birds. It is cultured to obtain protease for use in laundry detergent. Other applications that have been explored include use in synthesis of gold nanoparticles and as an agent to fight tooth decay.

*Clostridium* is a gram positive bacterium capable of forming spores and colonizing the intestines of humans and animals of agricultural importance such as cattle, poultry, and swine. There are a variety of *Clostridium* species that are troublesome pathogens in both humans and animals. Not only do the bacteria themselves present problems in terms of their pathogenicity, they also produce toxins that can cause extremely adverse health effects in humans and animals. In humans, the *Clostridium* bacteria from the species *botulinum* produces the botulism toxin that can cause muscle paralysis; the *perfringens* species causes food poisoning and gas gangrene in people and enterotoxaemia in sheep and goats; the tetani species causes tetanus, resulting in lockjaw or spastic paralysis in humans, cattle, dogs and other animals; the *sordelli* species causes pneumonia, endocarditis, arthritis, peritonitis and myonecrosis, as well as toxic shock syndrome.

The *difficile* species is of concern to humans and animals for colitis. It is capable of colonizing the intestines of humans and animals, including horses, cattle, poultry and swine. Much foodborne illness is also linked to *C. difficile*. In humans, *C. difficile* is most commonly known for its ability to cause disease in hospitalized patients who are being treated with antibiotics or chemotherapy for an infection from another bacterium. During this time, exposure to *C. difficile*, which is resistant to many common antibiotics, takes advantage of the reduction of colonic flora, growing rapidly and causing severe diarrhea, bloating, and abdominal pain.

Many cases of *C. difficile* infection have been reported from non-hospitalized patients where the source is believed to be mainly foodborne illness. *C. difficile* has been isolated from animal fecal samples of agricultural importance such as cattle, poultry, and swine and also from food products which come from these produce. This link is believed to be the source of many cases of foodborne illness.

Accordingly, new and effective methods to inhibit *C. difficile* and other clostridium species, along with new and effective methods to prevent them from producing the harmful toxins are desired.

SUMMARY OF THE DISCLOSURE

A novel strain of *Bacillus licheniformis* has been identified and isolated, namely *Bacillus licheniformis* strain OBT618. This strain is characterized by its ability to inhibit the growth and/or activity of bacteria of the genus *Clostridium*, including species which are pathogens and opportunistic pathogens through production through its own growth and/or through production of inhibitory substances such as enzymes, metabolites, and/or antibiotics.

The novel strain of *Bacillus licheniformis* can be used in numerous applications including contacting a pathogen of *Clostridium* with an effective amount of the bacillus strain to provide an inhibitory effect.

BRIEF DESCRIPTION OF THE DRAWING

FIG. 1 is the relevant sequence (SEQ. ID NO. 1) for *Bacillus licheniformis* strain OBT618.

DETAILED DESCRIPTION

It has been discovered that the novel *Bacillus licheniformis* strain OBT618 exhibits an inhibitory effect on pathogens of *Clostridium* and has many applications that can improve safety and reduce incidents of disease in humans and animals.

The term "inhibit" means to reduce or arrest growth and/or reproduction of *Clostridium* species, and/or to reduce or arrest production by and/or secretion of toxins from *Clostridium*. The term "inhibit" also encompasses killing *Clostridium* species and/or reducing or arresting the pathogenic or toxic effects of *Clostridium* species.

The term "effective amount" means an amount that will achieve a desired inhibitory effect to reduce incidents of diseases caused by pathogens of *Clostridium*. Effective amounts for particular applications can be determined by routine experimentation.

The novel strain of bacterium produces specific types of useful enzymes, metabolites and antibiotics to inhibit both the growth and toxin production from *Clostridium* species. These enzymes, metabolites and antibiotics reduce the potential for illness and disease by using the OBT618 bacterium.

Examples of *Clostridium* species that are inhibited by *Bacillus licheniformis* strain OBT618 include *C. botulinum*, *C. perfringens*, *C. tetani*, *C. sordelli*, *C. difficile* (including CDT A and CDT B).

The OBT618 bacteria can be used in various processes for inhibiting pathogenic or other undesirable or nuisance microorganisms such as *Clostridium* species, *C. difficile* species, *vibrio*, *E. coli* species, and *salmonella* species, by direct contact or by contacting the undesirable microorganism with one or more enzymes, metabolites, and/or antibiotics produced by *Bacillus licheniformis* strain OBT618. The process can be used to treat contaminated or potentially contaminated liquids and semi-solid materials such as wastewater, waste lagoons, manure piles, livestock pens, animal feed, animal feces and other animal waste, meat and other food processing facility water, pond, etc.

The OBT618 bacterium can be used to treat wastewater contaminated with *C. difficile* by spraying, direct inoculation of a liquid or a powder or a block containing the bacteria to reduce the *C. difficile* contamination and to reduce the toxins that may be present from the *C. difficile* or other *Clostridium* species.

Waste lagoons, manure piles, and pens containing waste from pig, cattle, sheep, chicken and equine can be treated with the novel OBT618 by spraying or dispersing in a powder form the bacteria to reduce the *C. difficile* contamination and to reduce the toxins that may be present from the *C. difficile* or other *Clostridium* species.

Animal feed can be treated by using the novel OBT618 bacterium as a direct fed microbial to either mix with the feed or as a separate feed supplement to reduce intestinal *C. difficile* colitis outbreaks and to reduce internal toxin production by *Clostridium* species.

Animal water can be treated by using the novel OBT618 bacterium to reduce the abundance and spread of *C. difficile* in drinking water and to inoculate the animal's intestinal tract to reduce intestinal *C. difficile* colitis outbreaks and to reduce internal toxin production by *Clostridium* species.

Chicken litter or other animal litter can be treated by using the novel OBT618 bacterium to spray the litter to reduce intestinal *C. difficile* colitis outbreaks and to reduce internal toxin production by *Clostridium* species in the animal.

Meat processing or food processing facility waste can be treated with the novel OBT618 bacterium by spraying, direct inoculation of a liquid or a powder or a block containing the bacterium to reduce the *C. difficile* contamination and to reduce the toxins that may be present from the *C. difficile* or other *Clostridium* species.

Farm ponds can be treated with the novel OBT618 by spraying, direct inoculation of a liquid or a powder or a block containing the bacteria to reduce the *C. difficile* contamination and to reduce the toxins that may be present from the *C. difficile* or other *Clostridium* species.

The disclosed *Bacillus licheniformis* strain OBT618 can be biologically purified and/or provided in a dried, sporulated form (e.g., in a particulate or powder form), or in a liquid composition. Such liquid or dry compositions may comprise various additives such as nutrients, dispersants, stabilizers, fragrances and dyes.

The described embodiments are preferred and/or illustrated, but are not limiting. Various modifications are considered within the purview and scope of the appended claims.

The *Bacillus licheniformis* strain OBT618 was deposited under the Budapest Treaty and will be irrevocably and without restriction or condition released to the public upon issuance of a patent. The *Bacillus licheniformis* strain OBT618 was deposited May 29, 2015 at the American Type Culture Collection (ATCC), P.O Box 1549, Manassas. Virginia 20108 and given accession number PTA-122188.

What is claimed is:

1. A process for inhibiting *Clostridium* comprising adding to a material selected from animal waste, animal feed and food processing facility waste, which material is contaminated with *Clostridium* an effective amount of a composition comprising dried sporulated *Bacillus licheniformis* strain OBT618 as deposited with the American Type Culture Collection under accession number PTA-122188 that produces enzymes, metabolites and antibiotics that inhibit growth and toxin production of *Clostridium* species, and at least one additive selected from the group consisting of dispersants, fragrances and dyes, wherein the *Bacillus licheniformis* strain OBT618 has the nucleotide sequence SEQ ID NO. 1.

2. The process of claim 1 wherein the composition powder.

* * * * *

```
SEQUENCE LISTING

<160> NUMBER OF SEQ ID NOS: 1

<210> SEQ ID NO 1
<211> LENGTH: 536
<212> TYPE: DNA
<213> ORGANISM: Bacillus licheniformis

<400> SEQUENCE: 1
tggagagttt gatcctggct caggacgaac gctggcggcg tgcctaatac atgcaagtcg       60
agcggaccga cgggagcttg ctcccttagg tcagcggcgg acgggtgagt aacacgtggg      120
taacctgcct gtaagactgg gataactccg ggaaaccggg gctaataccg gatrcttgat      180
tgaaccgcat ggttcaatta taaaggtgg cttttagcta ccacttacag atggacccgc      240
ggcgcattag ctagttggtg aggtaacggc tcaccaaggc aacgatgcgt agccgacctg      300
agagggtgat cggccacact gggactgaga cacggcccag actcctacgg gaggcagcag      360
tagggaatct tccgcaatgg acgaaagtct gacggagcaa cgccgcgtga gtgatgaagg      420
ttttcggatc gtaaaactct gttgttaggg aagaacaagt accgttcgaa tagggcggta      480
ccttgacggt acctaaccag aaagccacgg ctaactacgt gccagcagcc gcggta         536
```